(12) United States Patent
Chu et al.

(10) Patent No.: US 10,130,605 B2
(45) Date of Patent: Nov. 20, 2018

(54) COMPOSITIONS FOR USE IN TREATING INFLAMMATORY BOWEL DISEASES AND INTESTINAL COLITIS

(71) Applicant: TaiRx Inc., Taipei (TW)

(72) Inventors: Yi-Wen Chu, New Taipei (TW); Du-Shieng Chien, Guilford, CT (US)

(73) Assignee: TAIRX, INC., Taipei (TW)

( * ) Notice: Subject to any disclaimer, the term of this patent is extended or adjusted under 35 U.S.C. 154(b) by 0 days.

(21) Appl. No.: 15/867,201

(22) Filed: Jan. 10, 2018

(65) Prior Publication Data

US 2018/0200217 A1 Jul. 19, 2018

Related U.S. Application Data

(60) Provisional application No. 62/567,889, filed on Oct. 4, 2017, provisional application No. 62/447,892, filed on Jan. 18, 2017.

(51) Int. Cl.
*A61K 31/216* (2006.01)
*A61K 31/196* (2006.01)
*A61P 1/00* (2006.01)

(52) U.S. Cl.
CPC .......... *A61K 31/216* (2013.01); *A61K 31/196* (2013.01); *A61P 1/00* (2018.01)

(58) Field of Classification Search
CPC ........ A61K 31/196; A61K 31/216; A61P 1/00
See application file for complete search history.

(56) References Cited

U.S. PATENT DOCUMENTS

2002/0128317 A1* 9/2002 Charbit .................. A61K 31/00
 514/548
2009/0155277 A1* 6/2009 Odani ................ A61K 31/7088
 424/139.1

FOREIGN PATENT DOCUMENTS

WO WO-2009047801 A1 * 4/2009 ........... A61K 9/2077
WO 2017031161 A1 2/2017

OTHER PUBLICATIONS

Villadolid et al. "Immune checkpoint inhibitors in clinical practice: updated on management of immune-related toxicities" Translational lung cancer research, vol. 4, No. 5, Oct. 2015.

(Continued)

*Primary Examiner* — Savitha M Rao
(74) *Attorney, Agent, or Firm* — Hsiu-Ming Saunders; Intellectual Property Connections, Inc.

(57) ABSTRACT

Compositions for use in treating and/or alleviating a symptom of inflammatory bowel disease, colitis, and/or enterocolitis in a subject in need thereof are disclosed. The composition comprises a therapeutically effective amount of an anthraquinone derivative or a pharmaceutically acceptable salt thereof; and a pharmaceutically acceptable vehicle. In one embodiment, the composition comprises diacerein. Also disclosed is a first composition comprising an anthraquinone derivative selected from the group consisting of diacerein, aloe-emodin, emodin, and rhein, and a first pharmaceutically acceptable vehicle; and a second composition comprising mesalazine, and a second pharmaceutically acceptable vehicle, in combination for use in treating and/or alleviating a symptom of inflammatory bowel disease, colitis, and/or enterocolitis.

18 Claims, 9 Drawing Sheets

(56) References Cited

OTHER PUBLICATIONS

Kumar et al. "Current Diagnosis and Management of Immune Related Adverse Events (irAEs) Induced by Immune Checkpoint Inhibitor Therapy" Frontiers in Pharmacology, 8:49, 2017.
Carlos H. Barcenas and Nuhad K. Ibrahim "Chemotherapy-Induced Colitis", Chapter 6 from book "Colitis", published by Intech Open, [retrieved on Oct. 3, 2017] Downloaded from the internet: http://www.intechopen.com/books/colitis.

* cited by examiner

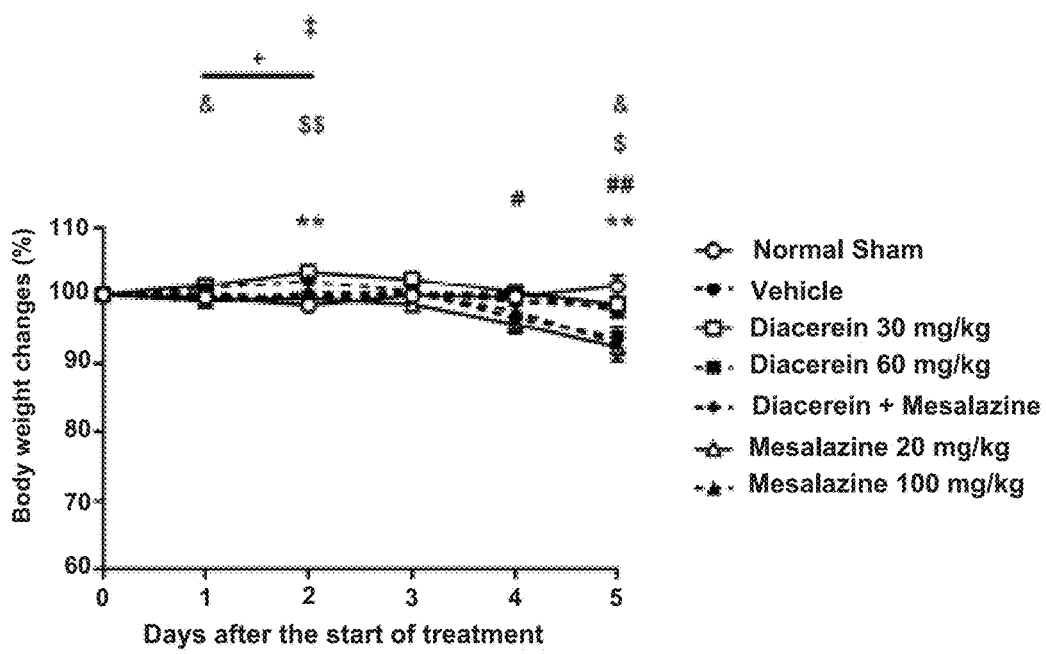

Normal Sharm vs Vehicle
***: p<0.001
****: p<0.0001

Vehicle vs Diacerein 60 mg/kg
$: p<0.05

Vehicle vs Mesalazine 100 mg/kg
‡: p<0.05
‡‡: p<0.01

Normal Sharm vs Vehicle
**: p<0.01

Vehicle vs Diacerein 30 mg/kg
: p<0.05

Vehicle vs Diacerein 60 mg/kg
$: p<0.05

Vehicle vs Diacerein + Mesalazine
&&: p<0.05

Vehicle vs Mesalazine 20 mg/kg
++: p<0.01

Vehicle vs Mesalazine 100 mg/kg
‡: p<0.05

Normal Sharm vs Vehicle
**: p<0.01
***: p<0.001
****: p<0.0001

Vehicle vs Mesalazine 100 mg/kg
‡‡: p<0.01

Normal Sharm vs Vehicle
***: p<0.001
****: p<0.0001

Vehicle vs Diacerein 60 mg/kg
$: p<0.05

Vehicle vs Diacerein + Mesalazine
&: p<0.05
&&: p<0.01

Vehicle vs Mesalazine 20 mg/kg
+: p<0.05

Vehicle vs Mesalazine 100 mg/kg
‡: p<0.05
‡‡: p<0.01

COMPOSITIONS FOR USE IN TREATING INFLAMMATORY BOWEL DISEASES AND INTESTINAL COLITIS

REFERENCE TO RELATED APPLICATION

The present application claims the priority to U.S. Provisional Application Ser. Nos. 62/447,892, filed Jan. 18, 2017, and 62/567,889, filed Oct. 4, 2017, all of which are herein incorporated by reference in their entireties.

FIELD OF THE INVENTION

The present invention relates generally to compositions for use in treating inflammatory bowel diseases, and more specifically to compositions comprising diacerein for use in treating ulcerative colitis, Crohn's disease, acute intestinal colitis, inflamed anus or rectum.

BACKGROUND OF THE INVENTION

Inflammatory bowel disease (IBD) is a condition that involves chronic inflammation in all or part of the digestive tract. Often painful and debilitating, IBD can lead to life-threatening complications as well as increase the risk for colon cancer. Other types of intestinal colitis, such as Immunotherapy-Induced Colitis, Immunotherapy-Induced Enterocolitis. Immune-Related Colitis, Chemotherapy-Induced Colitis, Taxane-Induced (ischemic) Colitis, and Chemotherapy-Induced Neutropenic. Enterocolitis, are commonly observed in patients who receive immunotherapy with drugs such as CTLA-4 inhibitors, PD-1/PD-L1 inhibitors, and/or other biological antibodies, etc. for the treatment of various cancer and immune-related diseases. Similar gastro-intestinal colitis is often observed after cancer patients receive single or multiple chemotherapeutic treatment like administration of taxanes. The two most common forms of IBD are ulcerative colitis and. Crohn's disease. In Crohn's, inflammation can occur anywhere in the digestive tract, from the mouth to the anus. By contrast, ulcerative colitis only involves inflammation of the large intestine, or colon. They are two distinct conditions, but there's a lot of overlap of the symptoms and physiology.

It is estimated that as many as 1 million Americans and Europeans suffer from IBD, and most sufferers begin to feel symptoms between the ages of 15 and 30. In addition, the estimated number of patients suffered from other types of above mentioned intestinal colitis could be as many as several millions.

With IBD, the intestines (small, large, and bowels) become inflamed, including redness, swelling, and mucosal lesion. Related symptoms, which can range from mild or severe, include severe or chronic abdominal pain, diarrhea, often bloody, sudden weight loss, lack of appetite, and rectal bleeding. Treatment for IBD varies per patient. Some may require medication, which can range from corticosteroids to biologic therapies and antibiotics. For example, the drug Mesalamine, delivered as either a rectal enema, suppository or pill, works to open up the small intestine. Intestinal colitis in general result in similar symptoms as observed in IBD patients, but commonly with compromised immune system.

Conditions of IBD and severe intestinal colitis are not curable, but if patients get on the appropriate medications, they can feel well. Thus, a need exists in the art to address better medications for treatment of both IBD and other types of intestinal colitis.

SUMMARY OF THE INVENTION

In one aspect, the invention relates to a composition comprising:
(a) a therapeutically effective amount of an anthraquinone derivative of formula (I):

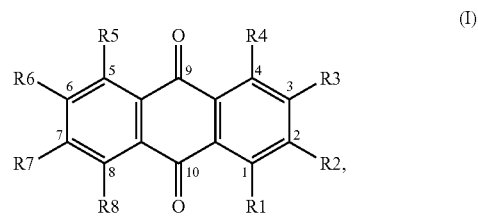

or a pharmaceutically acceptable salt thereof; and
(b) a pharmaceutically acceptable vehicle,
for use in treating and/or alleviating a symptom of inflammatory bowel disease, colitis, and/or enterocolitis in a subject in need thereof,
wherein:
R1 is H, or —O—C(=O)CH$_3$;
R2 is H, —OH, —(CH2)$_n$—OH, —C(=O)OH, n=1-8;
R3 is H, or —C(=O)OH;
R4 is H, or —OH;
R5 is H, or —OH;
R6 is H;
R7 is H, CH3;
R8 is H, or —O—C(=O)CH3.
In one embodiment of the invention, wherein:
R1 is H, or —O—C(=O)CH$_3$;
R2 is H, —OH, —CH2-OH, or —C(=O)O—H;
R3 is H. or —C(=O)OH;
R4 is H, or —OH;
R5 is H, or —OH;
R6 is H;
R7 is H, CH3;
R8 is H, or —O—C(=O)CH3.
In another embodiment, the symptom is at least one selected from the group consisting of a body weight loss, colon length shortening, a colon weight loss, occult blood positivity, loose stools, and diarrhea.

In another embodiment, the anthraquinone derivative is selected from the group consisting of diacerein, aloe-emodin, emodin, and rhein.

In another embodiment, the anthraquinone derivative is diacerein.

In another embodiment, a composition for use according to the invention is simultaneously in combination with an additional or a second composition comprising a therapeutically effective amount of mesalazine and a pharmaceutically acceptable vehicle for use in treating and/or alleviating a symptom of inflammatory bowel disease, colitis, and/or enterocolitis.

In another embodiment, a composition for use according to the invention is in combination with an additional or a second composition comprising a therapeutically effective amount of mesalazine and a pharmaceutically acceptable vehicle for use in treating and/or alleviating a symptom of inflammatory bowel disease, colitis, and/or enterocolitis.

In another embodiment, a composition for use according to the invention further comprises an additional or a second composition comprising a therapeutically effective amount of mesalazine and a pharmaceutically acceptable vehicle for use in treating and/or alleviating a symptom of inflammatory bowel disease, colitis, and/or enterocolitis in a subject in need thereof.

In another embodiment, the composition comprising mesalazine for use is in advance of the composition comprising diacerein for use.

In another embodiment, the composition comprising mesalazine for use and the composition comprising diacerein for use is at least one day apart.

In another aspect, the invention relates to a first composition comprising a therapeutically effective amount of an anthraquinone derivative selected from the group consisting of diacerein, aloe-emodin, emodin, and rhein, and a first pharmaceutically acceptable vehicle; and a second composition comprising a therapeutically effective amount of mesalazine, and a second pharmaceutically acceptable vehicle, in combination for use in treating and/or alleviating a symptom of inflammatory bowel disease, colitis, and/or enterocolitis in a subject in need thereof.

In one embodiment, the inflammatory bowel disease, colitis, and/or enterocolitis is at least one selected from the group consisting of ulcerative colitis, Crohn's disease, acute intestinal colitis, immunotherapy-induced colitis, immunotherapy-induced enterocolitis, immune-related colitis, chemotherapy-induced Colitis, taxane-induced (ischemic) colitis, chemotherapy-induced neutropenic enterocolitis, and inflamed anus or rectum.

In another embodiment, the colitis is at least one selected from the group consisting of microscopic colitis, diverticulosis-associated colitis, collagenous colitis, lymphocytic colitis, or Behçet's disease.

In another embodiment, a human daily dose of mesalazine is no less than 100 mg/kg×(0.020 in kg/human weight in kg)$^{0.33}$.

In another embodiment, a human daily dose of diacerein, aloe-emodin, emodin, or rhein is no less than 30 mg/kg×(0.020 in kg/human weight in kg)$^{0.33}$.

Alternatively, the invention relates to a method for treating and/or alleviating a symptom of inflammatory bowel disease, colitis, and/or enterocolitis in a subject in need thereof, comprising the step of: administering to the subject in need thereof a composition comprising:

(a) a therapeutically effective amount of an anthraquinone derivative of formula (I):

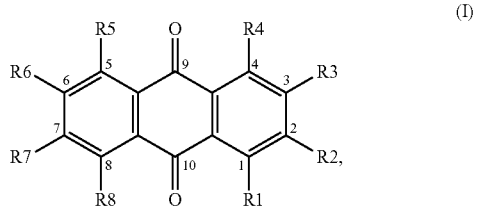

or a pharmaceutically acceptable salt thereof; and
(b) a pharmaceutically acceptable vehicle,
wherein:
R1 is H, or —O—C(=O)CH$_3$;
R2 is H, —OH, —(CH2)$_n$—OH, —C(=O)OH, n=1-8;
R3 is H, or —C(=O)OH;
R4 is H, or —OH;
R5 is H, or —OH;
R6 is H;
R7 is H, CH3;
R8 is H, or —O—C(=O)CH3.

In one embodiment, the method further comprises the step of: administering to the subject in need thereof an additional or a second composition comprising a therapeutically effective amount of mesalazine and a pharmaceutically acceptable vehicle.

In another embodiment, the step of administering the composition comprising mesalazine is performed simultaneously with the step of administering the composition comprising diacerein.

In another embodiment, the step of administering the composition comprising mesalazine is performed in advance of the step of administering the composition comprising diacerein In another embodiment, the step of administering the composition comprising mesalazine and the step of administering the composition comprising diacerein is performed at least one day apart.

The invention also relates to a method for treating and/or alleviating a symptom of inflammatory bowel disease, colitis, and/or enterocolitis in a subject in need thereof, comprising:

administering to the subject in need thereof a first composition comprising a therapeutically effective amount of an anthraquinone derivative selected from the group consisting of diacerein, aloe-emodin, emodin, and rhein, and a first pharmaceutically acceptable vehicle; and a second composition comprising a therapeutically effective amount of mesalazine, and a second pharmaceutically acceptable vehicle.

In one embodiment, the composition comprising mesalazine is administered to the subject in need thereof in advance of the composition comprising diacerein.

In another embodiment, the composition comprising mesalazine is administered to the subject in need thereof simultaneously with the composition comprising diacerein.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows body weight changes.

DETAILED DESCRIPTION OF THE INVENTION

Figure 2A:
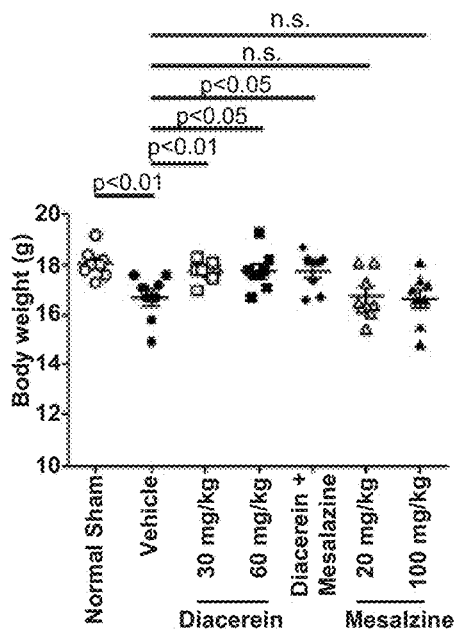
FIG. 2A shows body weight.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

"An effective amount" refers to the amount of an active agent that is required to confer a therapeutic effect on the treated subject. Effective doses will vary, as recognized by those skilled in the art, depending on routes of administration, excipient usage, and the possibility of co-usage with other therapeutic treatment.

The term "treating" or "treatment" refers to administration of an effective amount of a therapeutic agent to a subject, who has a disease, or a symptom or predisposition toward such a disease, with the purpose to cure, alleviate, relieve, remedy, ameliorate, or prevent the disease, the symptoms of it, or the predispositions towards it.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

The invention relates to the discovery of the pharmacological effects of test substances (such as Diacerein and Mesalazine) on dextran sodium sulfate (DSS)-induced acute colitis in mouse. The invention relates to diacerein and its analogues for use in treating or alleviating a symptom of irritable bowel disease, colitis, and/or enterocolitis in a patient in need thereof. In one embodiment, the invention relates to diacerein alone or in combination with mesalazine for use in treating, or alleviating a symptom of ulcerative colitis, Crohn's disease, acute intestinal colitis, immunotherapy-induced colitis, immunotherapy-induced enterocolitis, immune-related colitis, chemotherapy-induced Colitis, taxane-induced (ischemic) colitis, chemotherapy-induced neutropenic enterocolitis, or inflamed anus or rectum.

The exemplified test substances shown in Table 1 are: Aloe-emodin (1,8-Dihydroxy-3-(hydroxymethyl)anthraquinone, 3-Hydroxymethylchrysazine); Diacerein (1,8-Diacetoxy-3-carboxyanthraquinone); Emodin (1,3,8-Trihydroxy-6-methyl-9,10-anthracenedione, 1,3,8-Trihydroxy-6-methylanthraquinone, 6-Methyl-1,3,8-trihydroxyanthraquinone); Rhein (4,5-Dihydroxyanthraquinone-2-carboxylic acid, 9,10-Dihydro-4,5-dihydroxy-9,10-dioxo-2-anthracenecarboxylic acid); Mesalazine (5-Amino-2-hydroxybenzoic acid, 5-AS, 5-Aminosalicylic acid, Mesalamine).

TABLE 1

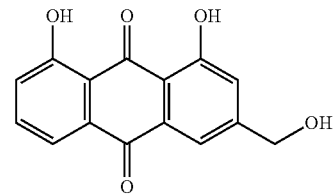 [SMILES: O=C1c2cccc(O)c2C(=O)c2c(O)cc(CO)cc21]

Aloe-emodin

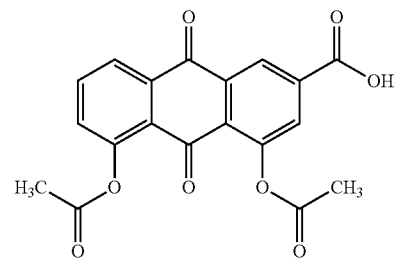 [SMILES: CC(=O)Oc1cccc2c1C(=O)c1c(OC(C)=O)cc(C(=O)O)cc1C2=O]

Diacerein

TABLE 1-continued

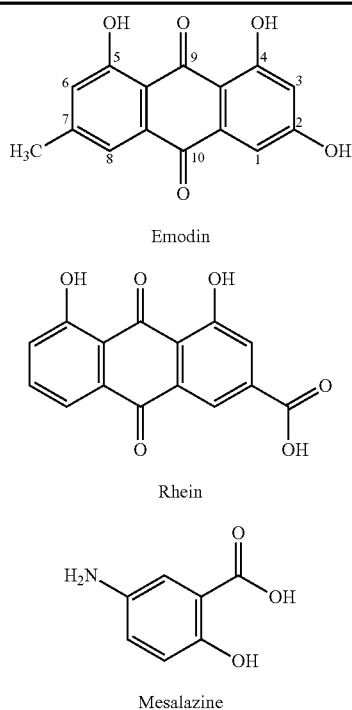

Emodin

Rhein

Mesalazine

Abbreviations.
DAI: Disease activity index;
DMSO: Dimethyl sulfoxide;
HE: Hematoxylin and eosin;
PO: Orally;
PEG: Polyethylene glycol;
QD: Once daily;
SEM: Standard error of the mean.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Test substances. Diacerein and Mesalazine were provided by TaiRx, Inc. To prepare dosing solution, Diacerein and Mesalazine were weighed and suspended with vehicle [2% DMSO/30% PEG400/0.5% TWEEN® 80/water (v/v)].

Induction of acute colitis. Acute colitis was induced by giving mice with 2.5% DSS (MP Biomedicals) in a drinking water for 5 consecutive days. The DSS administration was taken place in two separate days; where the mice were divided into two groups based on their body weight before the day of the DSS administration.

Route of drug administration. Diacerein, Mesalazine, and vehicle were administered via oral route in a dosing volume of 5 mL/kg.

Treatment doses. Diacerein was administered at 2 dose levels of 30 and 60 mg/kg, once daily for 5 days. Mesalazine was administered at 2 dose levels of 20 and 100 mg/kg, once daily for 5 days. Combination of Diacerein (30 mg/kg) and Mesalazine (20 mg/kg) was administered once daily for 5 days.

Animals. Eight-week-old female C57BL/6 mice were obtained from Japan SLC, Inc. (Japan). All animals used in the study were housed and cared in accordance with the Japanese Pharmacological Society Guidelines for Animal Use.

Environment. The animals were maintained in an animal facility under conventional conditions.

Animal husbandry. The animals were housed in TPX cages (CLEA Japan) with a maximum of 4 mice per cage. Sterilized Paper-Clean (Japan SLC) was used for bedding and replaced once a week.

Food and drink. Sterilized solid normal diet was provided to animals ad libitum, being placed in a metal lid on the top of the cage. Pure water or DSS-water was also provided ad libitum from a water bottle equipped with a rubber stopper and a sipper tube.

Animal and cage identification. Mice were identified by ear punch. Each cage was labeled with a specific identification code.

Measurement of disease activity index score. A disease activity index (DAI) was calculated daily by summation of the following parameters:
 (i) Weight loss (0=no weight loss; 1=1-5% weight loss; 2=6-10% weight loss; 3=11-15% weight loss; and 4=>15% weight loss);
 (ii) Occult blood positivity (0=no bleeding; 1=occult blood test (+); 2=occult blood test (++); 3=occult blood test (+++); and 4=gross bleeding from the anus); and
 (iii) Stool consistency (0=normal stools; 2=loose stools; 4=diarrhea).

Macroscopic scoring of colon tissue. Colonic damage was scored using the published criteria of measurement (Wallace et al, *Gastroenterology*, 1992, 102, 18-27).

Histological analyses. For HE staining, sections were cut from paraffin blocks of colon tissue prefixed in 10% neutral buffered formalin (Wako Pure Chemical Industries, Japan) and stained with Lillie-Mayer's Hematoxylin (Muto Pure Chemicals Co., Ltd., Japan) and eosin solution (Wako Pure Chemical Industries). Representative photos of the changes observed were captured from each group.

Statistical tests. Statistical analyses were performed using unpaired one-tailed Student's t-test on GraphPad Prism 6 (GraphPad Software Inc., USA). P values <0.05 were considered statistically significant. Results were expressed as geometric mean±SEM.

Experimental Design and Treatment
Study Groups

Group 1: Normal Sham. Eight normal mice were fed with a normal regular diet and pure drinking water ad libitum without any treatment until day 4.

Group 2: Vehicle. Eight DSS-induced colitis mice were orally administered with vehicle [2% DMSO/30% PEG400/0.5% Tween80/water, v/v] in a dosing volume of 5 mL/kg once daily from day 0 to day 4.

Group 3: Diacerein 30 mg/kg. Eight DSS-induced colitis mice were orally administered with vehicle supplemented with Diacerein at a dose of 30 mg/kg, once daily from day 0 to 4.

Group 4: Diacerein 60 mg/kg. Eight DSS-induced colitis mice were orally administered with vehicle supplemented with Diacerein at a dose of 60 mg/kg, once daily from day 0 to 4.

Group 5: Diacerein+Mesalazine. Eight DSS-induced colitis mice were orally administered with vehicle supplemented with combination of Diacerein (30 mg/kg) and Mesalazine (20 mg/kg), once daily from day 0 to day 4.

Group 6: Mesalazine 20 mg/kg. Eight DSS-induced colitis mice were orally administered with vehicle supplemented with Mesalazine at a dose of 20 mg/kg, once daily from day 0 to 4.

Group 7: Mesalazine 100 mg/kg. Eight DSS-induced colitis mice were orally administered with vehicle supplemented with Mesalazine at a dose of 100 mg/kg, once daily from day 0 to 4.

Table 2 below summarizes the treatment schedule. The average body weight of mice is about 18-22 grams.

TABLE 2

| Group | No. mice | Mice | Test substance | Dose (mg/kg) | Volume (mL/kg) | Regimen | Sacrifice (day) |
|---|---|---|---|---|---|---|---|
| 1 | 8 | Normal Sham | — | — | — | — | 5 |
| 2 | 8 | DSS | Vehicle | — | 5 | PO, QD, Day 0-4 | 5 |
| 3 | 8 | DSS | Diacerein | 30 | 5 | PO, QD, Day 0-4 | 5 |
| 4 | 8 | DSS | Diacerein | 60 | 5 | PO, QD, Day 0-4 | 5 |
| 5 | 8 | DSS | Diacerein + Mesalazine | 30 20 | 5 5 | PO, QD, Day 0-4 | 5 |
| 6 | 8 | DSS | Mesalazine | 20 | 5 | PO, QD, Day 0-4 | 5 |
| 7 | 8 | DSS | Mesalazine | 100 | 5 | PO, QD, Day 0-4 | 5 |

Animal Monitoring and Sacrifice

The viability, clinical signs and behavior were monitored daily. Body weight was recorded before the treatment. Mice were observed for significant clinical signs of toxicity, moribundity and mortality approximately 60 minutes after each administration. Mice were sacrificed by exsanguinations through direct cardiac puncture under isoflurane anesthesia (Pfizer Inc.). Colon length and weight were measured from the end of the cecum to the anus.

The pharmacological effects of aloe-emodin, emodin, and rhein were also respectively tested using the same protocol described above.

Results

Body Weight Changes and General Condition (FIG. 1)

Mean acute body weight loss in the vehicle group was more significant than that in the Normal Sham group at Day 2 by 3.6%. Mean body weight loss in the vehicle group (−7.7%) was significant, as compared with that of the Normal Sham group at Day 5 (~1.4% increase from Day 0), suggesting a significant body weight loss in these animals after induced by DSS (p=0.002).

Both Mesalazine groups showed similar significant body weight loss as DSS-induced vehicle group by −8.5%−−9.0%% after the 5-day treatment (p=0.003), whereas Diacerein groups appeared to maintain the body weights close to the Sham animals, with much less body weight loss as compared with the Mesalazine-treated mice.

There were no dead animals in all groups during the treatment period. In the present study, none of the animals showed apparent deterioration in general health condition.

Body Weight on the Day of Sacrifice (FIG. 2A and Table 3)

The DSS-induced vehicle group showed significant decrease in body weight on the day of sacrifice than the Normal Sham group by 7.7%. Both Diacerein groups and the Diaserein+Mesalazine group showed significant increase in body weight on the day of sacrifice than the DSS-induced vehicle group by 6.6 and 6.0%, respectively. As compared with Normal Sham animals (~18.1 g), both Mesalazine 20 and 100 mg/kg groups showed significant body weight loss on the day of sacrifice (~16.7 g), similar to that observed in the DSS-induced vehicle group (16.7 g).

Figure 2B:
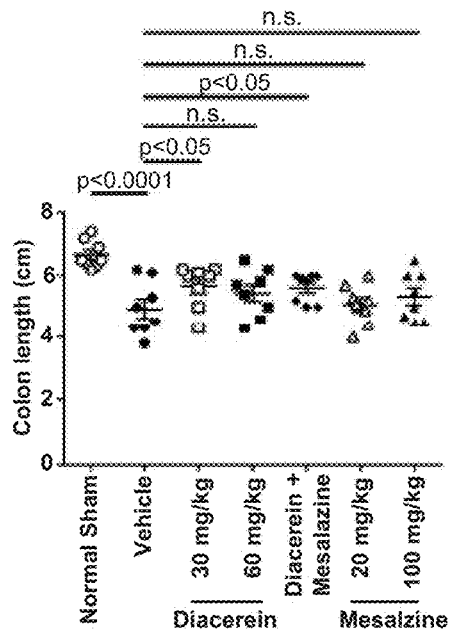
FIG. 2B shows colon length.
Figure 2C:
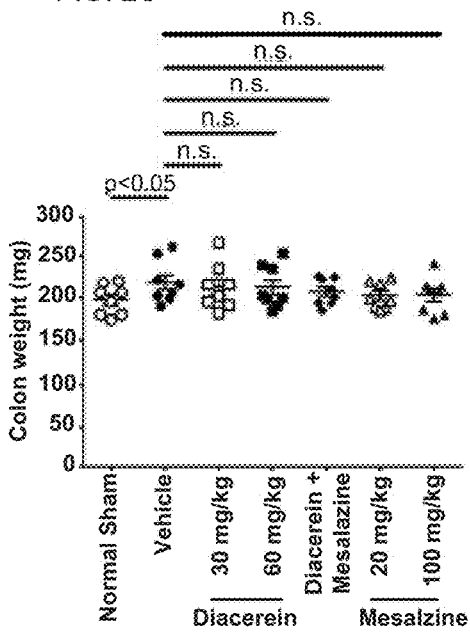
FIG. 2C shows colon weight.
Figure 2D:
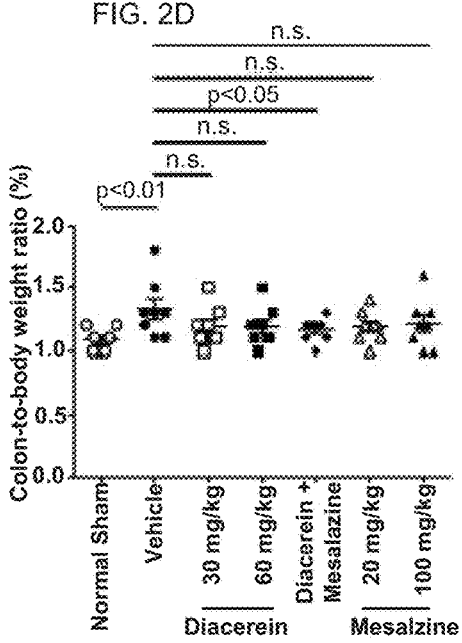
FIG. 2D shows colon-to-body weight ratio.

Colon Length, Colon Weight and Colon-to-Body Weight Ratio (FIGS. 2B-D and Table 3)

The DSS-induced vehicle group showed significant decrease in colon length than the Normal Sham group by 26.9% (from 6.7 to 4.9 cm). The Diacerein group at 30 and 60 mg/kg and the Diaserein+Mesalazine groups showed significant improvement in colon length than the DSS-induced vehicle group by 11-16%. Both Mesalazine groups showed effect on improving colon length by only 3-9%, where the observed effect was not statistically significant.

The DSS-induced vehicle group showed significant increase in colon weight than the Normal Sham group by 10.2% (from 197 to 217 mg). Although all treatment groups showed some effect (~2.8-6.9%) on reducing the colon weight increased by DSS, but the effect was not statistically significant.

However, normalized by the body weight, the DSS-induced vehicle group showed significant increase in colon-to-body weight ratio than the Normal Sham group ~19.6%. The Diaserein+Mesalazine combination group showed significant decrease in colon-to-body weight ratio than the DSS-induced vehicle group by 10.6% (p=0.049). Both Diacerein groups and both Mesalazine groups showed slight lower effect on colon-to-body weight ratio than the DSS-induced vehicle group by 7-9%, but the observed effects were not statistically significant Table 3 shows the results of body weight, colon length and colon weight in each group.

TABLE 3*

| parameter | Normal Sham | vehicle | Diacerein 30 mg/kg | Diacerein 60 mg/kg | Diacerein + Mesalazine | Mesalazine 20 mg/kg | Mesalazine 100 mg/kg |
|---|---|---|---|---|---|---|---|
| BW (g) | 18.1 ± 0.2 | 16.7 ± 0.3 | 17.8 ± 0.1 | 17.8 ± 0.3 | 17.7 ± 0.3 | 16.8 ± 0.3 | 16.6 ± 0.4 |
| Colon length | 6.7 ± 0.2 | 4.9 ± 0.3 | 5.6 ± 0.2 | 5.4 ± 0.3 | 5.6 ± 0.2 | 5.0 ± 0.2 | 5.3 ± 0.3 |
| Colon weight | 197 ± 6 | 217 ± 9 | 211 ± 10 | 211 ± 0.1 | 206 ± 6 | 202 ± 6 | 202 ± 8 |
| Colon-to-BW ratio | 1.1 ± 0.0 | 1.3 ± 0.1 | 1.2 ± 0.1 | 1.2 ± 0.1 | 1.2 ± 0.0 | 1.2 ± 0.0 | 1.2 ± 0.1 |

*The parameters were measured and data were represented as geometric mean ± SEM. There were 8 mice in each group (n = 8). BW: body weight (g); Colon length (cm); Colon weight (mg); Colon-to- BW ratio: colon-to-body weight ratio (%).

Disease Activity Index (FIGS. 3A-D)

DAI (FIG. 3A)

The DSS-induced vehicle group showed significant increases in DAI than the Normal Sham group in all 5-day induction period. DAI measurement in the Vehicle group was significantly increased from Day 1 (2.6) to Day 4/5 (6.4/7.1) compared with the Normal Sham group (normal index ~0.3-0.5). The Diacerein 30 and 60 mg/kg group showed an effective reduction in the DAI observed at Day 4 (~5.1) and Day 5 (~6.3). Whereas, the low dose of Mesalazine (20 mg/kg) showed no effect throughout 5-day treatment, and high dose of Mesalazine (100 mg/kg) group had no clear reduction in DAI at Day 4 or Day 5, but a significant reduction at Day 2 and 3. Diacerein+Mesalazine combination treatment had no effect in DAI reduction at Day 2-3 but some effect at day 4-5.

The DAI results revealed that the treatments of Diacerein and Mesalazine on DSS-induced animals were both effective but likely had different onset patterns. Mesalazine showed good effect in the first 2-3 days of treatment and gradually diminished in its activity after, while Diacerein appeared to be more effective at latter part of treatment (Day 4-5) than the early stage of the treatment. Diacerein seemed to be more effective than Mesalazine with lower effective dose level.

Figure 3A:
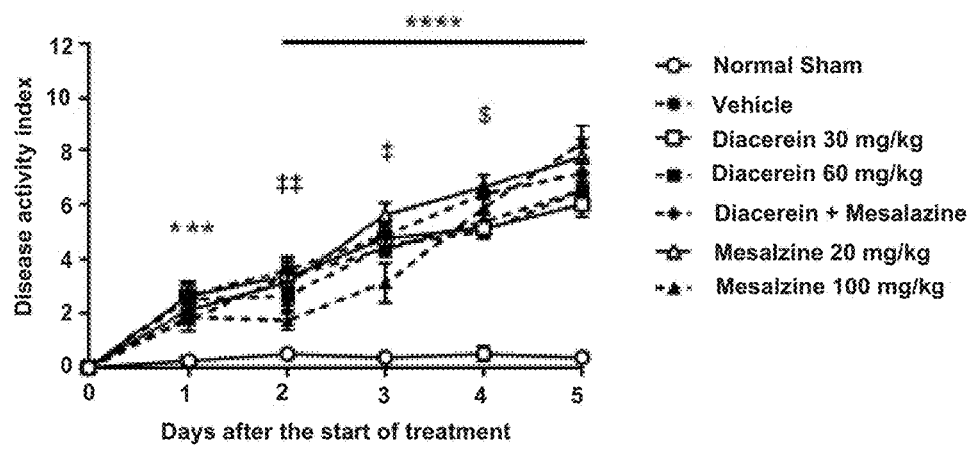
FIG. 3A shows disease activity index.
Figure 3B:
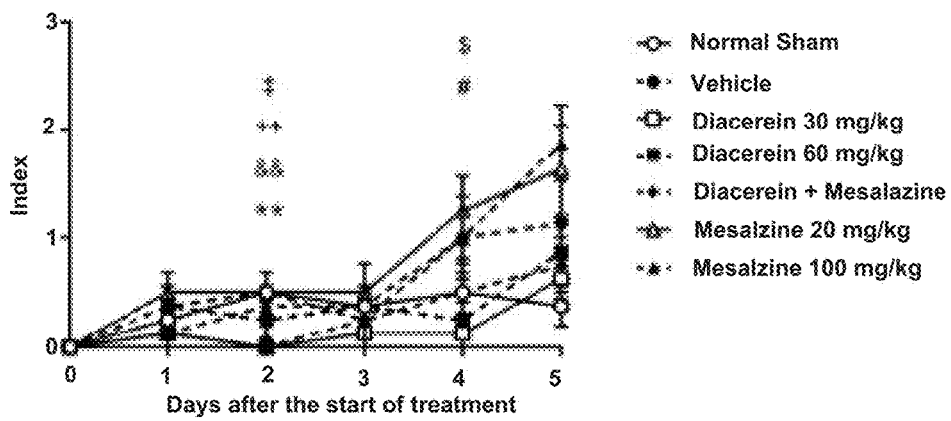
FIG. 3B shows body weight score.

Body Weight Score (FIG. 3B)

The effect of dosing on body weight score became clear at late stage of treatment (Day 4 and 5). Vehicle group had higher Body weight score (1.0/1.1) on Day 4/5, as compared with the Normal Sham (0.4-0.5). The Diacerein treatment groups were able to reduce the body weight score to 0.1-0.3 on Day 4 ($p<0.05$) and 0.6-0.9 on Day 5. In contrast, both Mesalazine groups increased the body weight score to 1.0-1.3 on Day 4 and 1.6-1.9 on Day 5, more severe than the DDS-induced animals. The Diacerein+Mesalazine combination groups appeared to be able to maintain the body weight score in the range of 0.5-0.8, close to the Normal Sham animals.

The results of Body weight score indicated the superior effect of Diacerein to Mesalazine in this DDS-induced acute colitis model. Diacerein showed ability in maintaining normal body weight throughout the treatment, whereas Mesalazine had no effect in reducing body weight score but causing the increase in body weight score greater than the DDS-induced control animals.

Figure 3C:
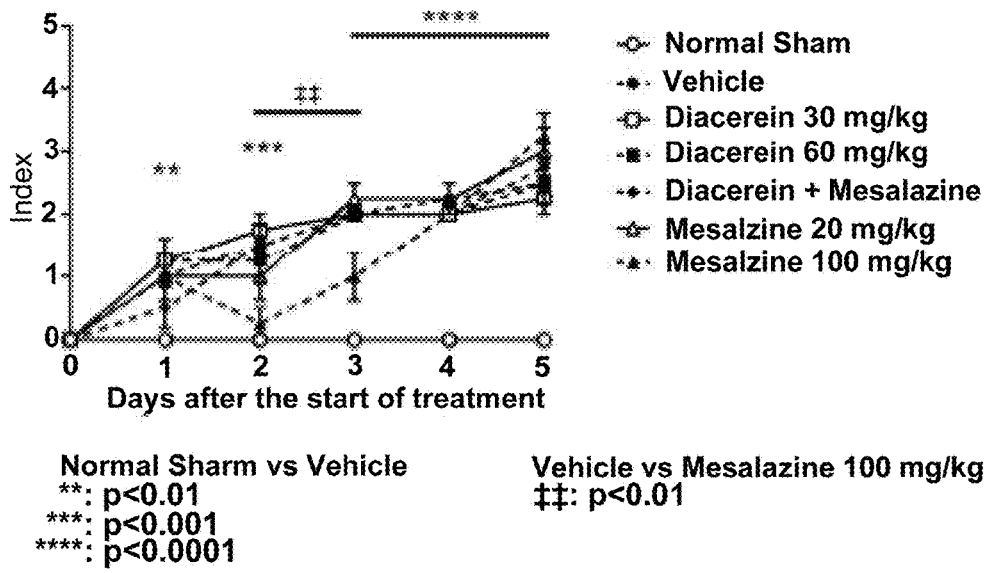
FIG. 3C shows diarrheal stool score.

Diarrheal Stool Score (FIG. 3C)

Diarrheal stool score measured in the Vehicle group was significantly higher in all 5-day induction period, compared with the Normal Sham group. Among all treatment groups, only the high dose of Mesalazine (100 mg/kg) group showed a significant reduction in the Diarrheal stool score observed at Day 2 and 3; while the effect on reducing diarrheal score apparently decreased on Day 4 and 5. There were no significant differences in the Diarrheal stool score between the Vehicle group and any of the other treatment groups.

Figure 3D:
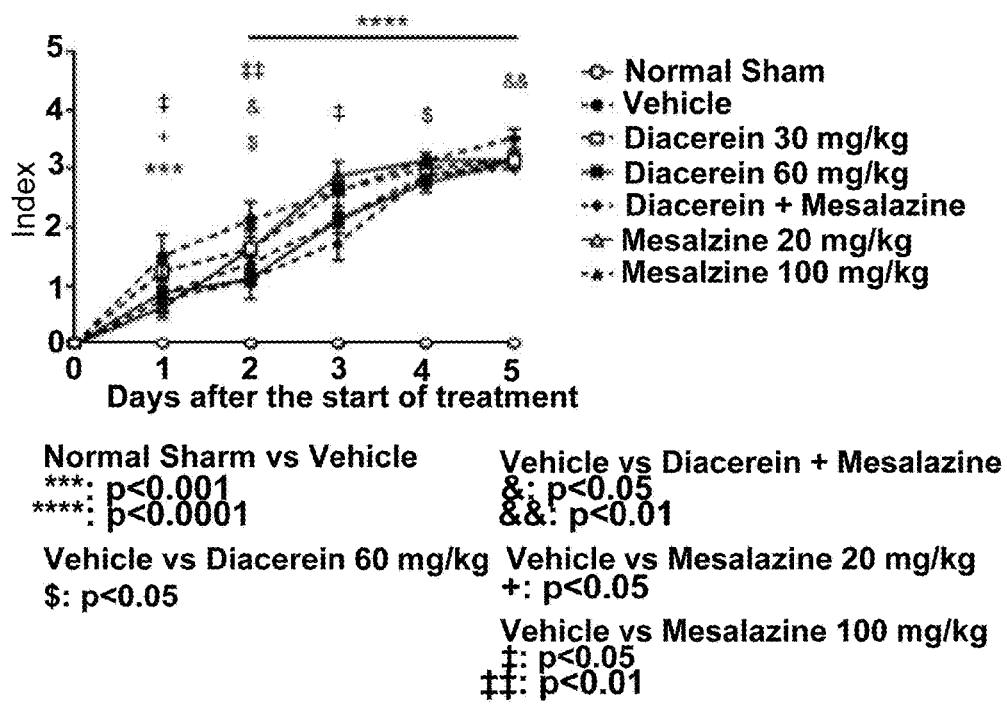
FIG. 3D shows fecal blood score.

Fecal Blood Score (FIG. 3D)

Significant fecal blood was observed in DDS-induced colitis animals. Fecal blood score measured in the DDS-induced Vehicle group was significantly increased from Day 1 to Day 5, as compared with the Normal Sham group. The low dose of Diacerein (30 mg/kg) decreased slight fecal blood, where the high dose of Diacerein (60 mg/kg) group showed more significant reduction in the fecal blood score compared with the Vehicle group observed during the treatment. Similar significant reduction in fecal blood was also observed in the Diacerein+Mesalazine combination group. The low dose Mesalazine 20 mg/kg group showed a significant reduction in the fecal blood score compared with the Vehicle group observed only at Day 1. The high dose of Mesalazine 100 mg/kg group showed a significant reduction in the fecal blood score compared with the Vehicle group observed at Day 1 to 3. In summary, both Diacerein and Mesalazine showed dose-proportional and significant effects on reducing the fecal blood in DDS-induced acute colitis animals.

At the end of treatment, the Diacerein+Mesalazine combination group showed significant decrease in fecal blood score than the DSS-induced vehicle group by 14.3% at Day 5. Both Diacerein groups and both Mesalazine groups showed reducing effect on fecal blood score than the DSS-induced vehicle group by 11.4% at Day 5, but the observed effects were not statistically significant.

Disease Activity Index (FIGS. 4A-F and Table 4)

Figure 4A:
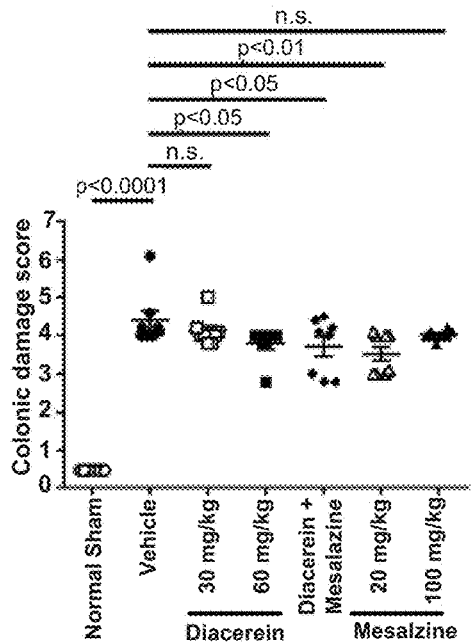
FIG. 4A shows colonic damage score.

Colonic Damage Score (FIG. 4A)

The DSS-induced vehicle group showed significant increase in colonic damage score than the Normal Sham group by 780%. The Diacerein 60 mg/kg, the Mesalazine 20 mg/kg and the Diacerein+Mesalazine groups showed significant decrease in colonic damage score than the DSS-induced vehicle group by 13.6, 20.5 and 15.9%, respectively ($p<0.05$). Although the Diacerein 30 mg/kg and the Mesalazine 100 mg/kg groups showed lower effect on colonic damage score than the DSS-induced vehicle group by 6.8 and 9.1%, respectively, but the observed effect was not statistically significant.

Figure 4B:
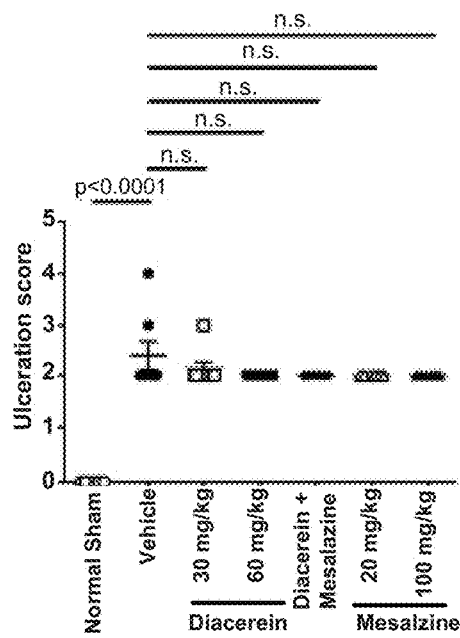
FIG. 4B shows ulceration score.

Ulceration Score (FIG. 4B)

The DSS-induced vehicle group showed significant increase in ulceration score than the Normal Sham group. Although all treatment groups showed lower effect on ulceration score than the DSS-induced vehicle group by 8.7-13.0%, but the observed effect was not statistically significant. Pharmacological effect of test compounds, including Mesalazine up to 100 mg/kg, on the intestinal ulceration induced by DDS appeared to be non-detectable in this disease model.

Figure 4C:
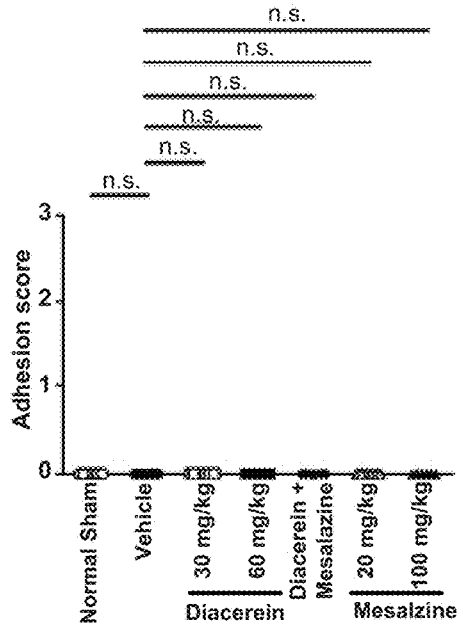
FIG. 4C shows adhesion score.

Adhesions Score (FIG. 4C)

The DSS-induced vehicle group showed similar adhesions score as the Normal Sham group. All treatment groups showed similar adhesions score as the DSS-induced vehicle group. Similar to above ulceration reduction measurement, effect of the test compounds, including Mesalazine, on the intestinal adhesion was non-detectable in this disease model.

Figure 4D:
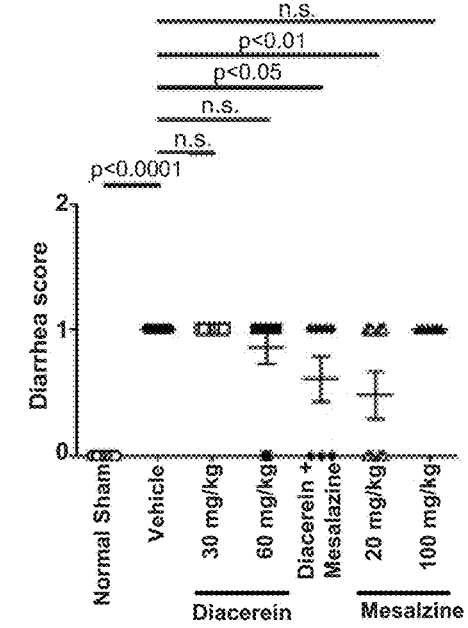
FIG. 4D shows diarrhea score.

Diarrhea Score (FIG. 4D)

The DSS-induced vehicle group showed significant increase in diarrhea score than the Normal Sham group. The Mesalazine 20 mg/kg and the Diacerein+Mesalazine groups showed significant decrease in diarrhea score than the DSS-induced vehicle group. Although the Diacerein 60 mg/kg group showed lower effect on diarrhea score than the DSS-induced vehicle group, but the observed effect was not statistically significant. The Diacerein 30 mg/kg and the Mesalazine 100 mg/kg groups showed similar diarrhea score as the DSS-induced vehicle group.

Figure 4E:
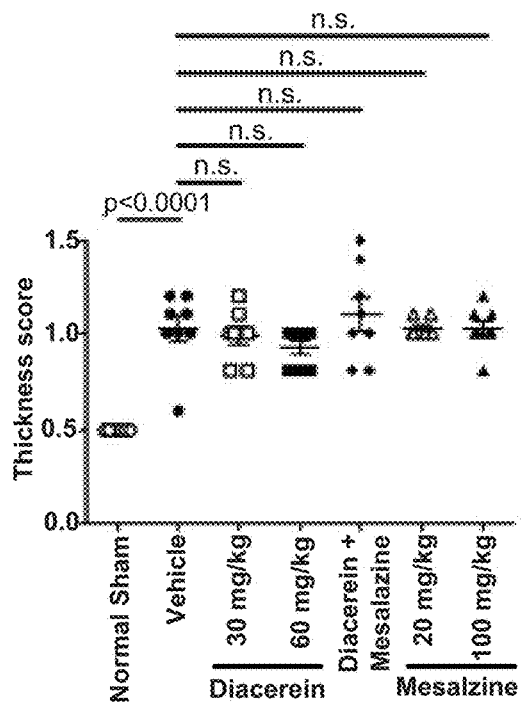
FIG. 4E shows thickness score.
Figure 4F:
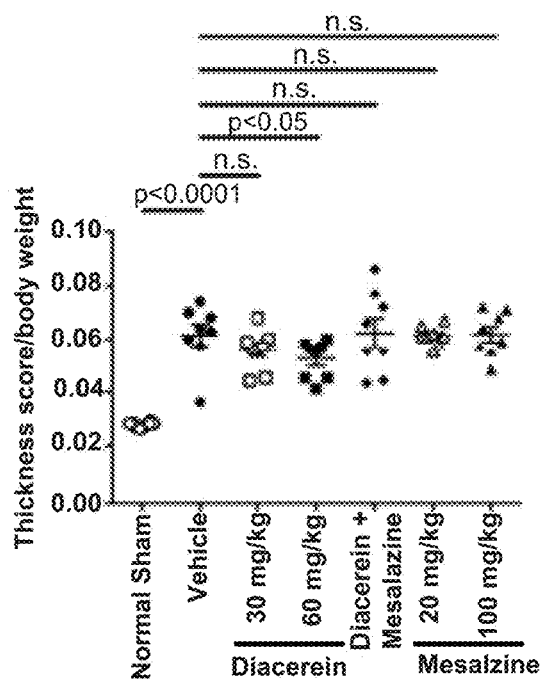
FIG. 4F shows normalized changes of colonic thickness.

Thickness Score (FIG. 4E)

The DSS-induced vehicle group showed significant increase in thickness score than the Normal Sham group by 100%. Although all treatment groups showed lower or higher effect on thickness score than the DSS-induced vehicle group by −10-10%, but the observed effect was not statistically significant.

Suggest to analyze body wt-normalized thickness score. Table 4 shows colonic damage score.

TABLE 4*

| parameter | Normal Sham | vehicle | Diacerein 30 mg/kg | Diacerein 60 mg/kg | Diacerein + Mesalazine | Mesalazine 20 mg/kg | Mesalazine 100 mg/kg |
|---|---|---|---|---|---|---|---|
| colonic damage | 0.5 ± 0.0 | 4.4 ± 0.3 | 4.1 ± 0.1 | 3.8 ± 0.1 | 3.7 ± 0.3 | 3.5 ± 0.2 | 4.0 ± 0.0 |
| ulceration | NC | 2.3 ± 0.3 | 2.1 ± 0.1 | 2.0 ± 0.0 | 2.0 ± 0.0 | 2.0 ± 0.0 | 2.0 ± 0.0 |
| adhesion | NC | NC | NC | NC | NC | NC | NC |
| diarrhea | NC | 1.0 ± 0.0 | 1.0 ± 0.0 | NC | NC | NC | 1.0 ± 0.0 |
| thickness | 0.5 ± 0.0 | 1.0 ± 0.1 | 1.0 ± 0.0 | 0.9 ± 0.0 | 1.1 ± 0.1 | 1.0 ± 0.0 | 1.0 ± 0.0 |

*NC: not calculated; Each parameter was measured and the result presented with the score.

Histological Analyses

Figure 5A:
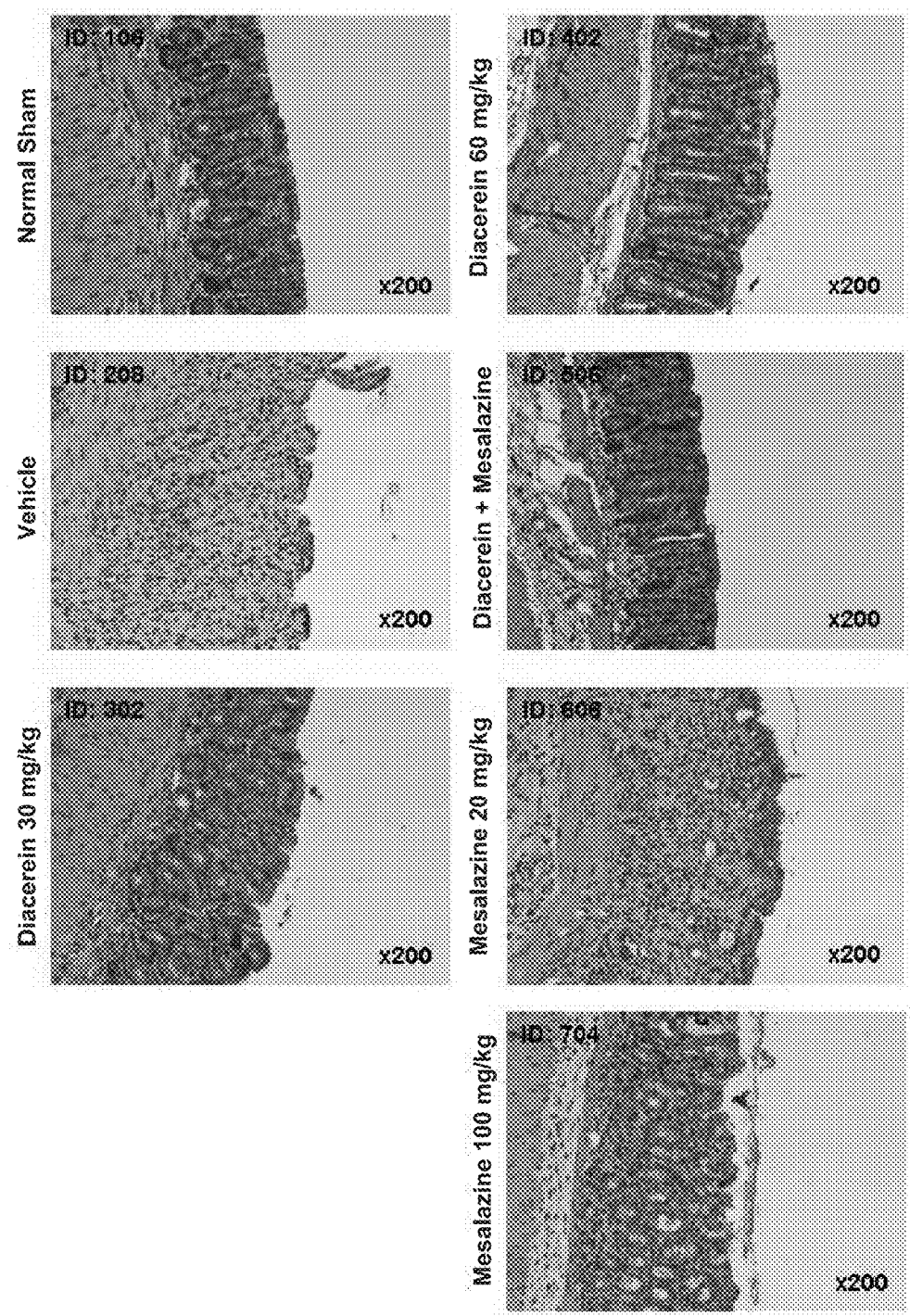
FIGS. 5A-C are representative photomicrographs of HE-stained colon sections.
Figure 5B:
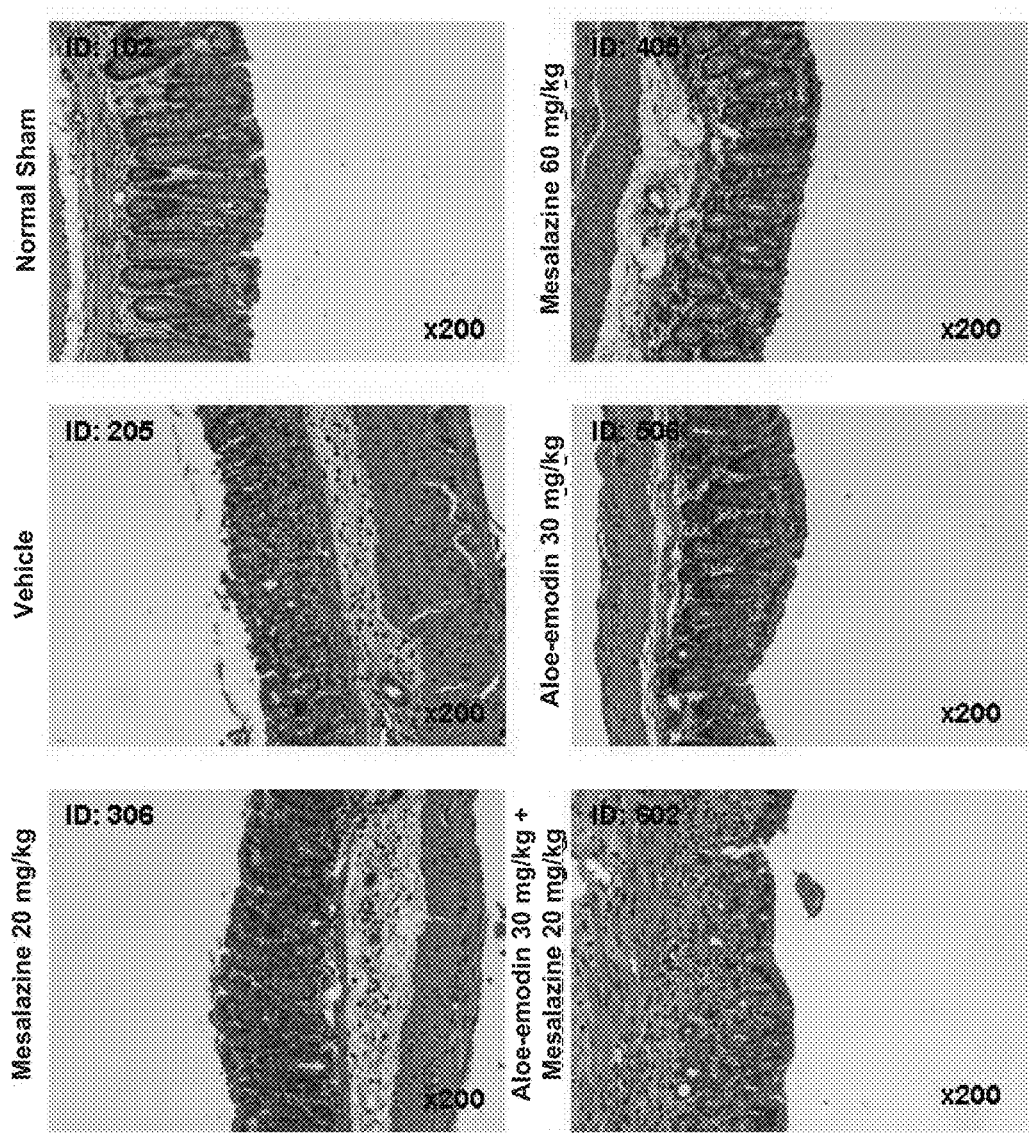
Figure 5C:
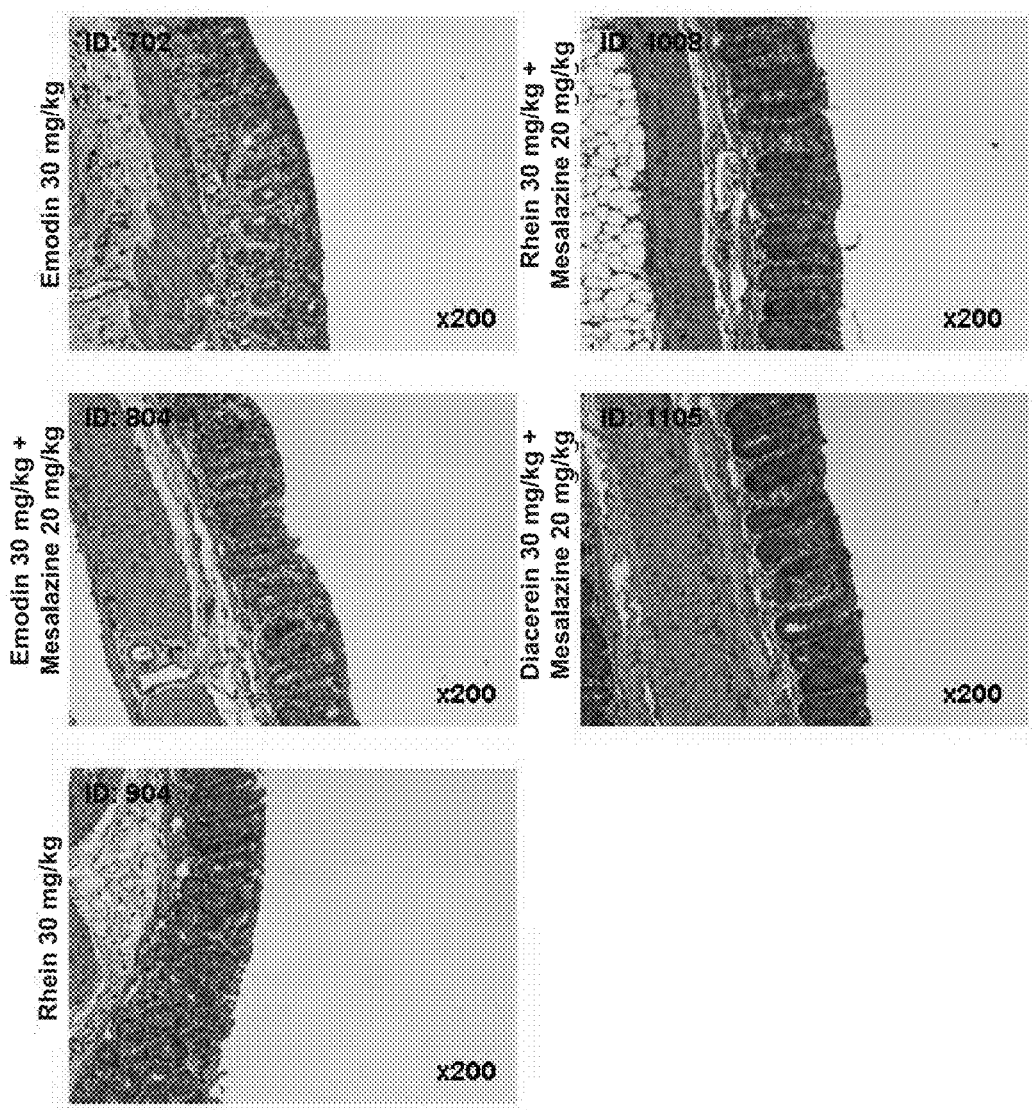

HE Staining (FIGS. 5A-C)

Representative photomicrographs of HE-stained colon sections are shown in FIGS. 5A-C. Colon sections from the Vehicle group exhibited loss of crypt and epithelium and inflammatory cell infiltration.

FIG. 5A shows a less loss of crypt and epithelium were observed in the Diacerein treatment groups and Diacerein+Mesalazine group compared with the Vehicle group. No significant effect on preventing the loss of intestinal crypt and epithelium was observed for Mesalazine treatment alone. The findings from HE staining on colonic membrane indicated much greater potency of Diacerein in healing colitis membrane damage than Mesalazine.

FIGS. 5B-C show a less loss of crypt and epithelium were observed in the Mesalazine treatment groups and the Aloe-emodin, the Rhein, the Rhein+Mesalazine and the Diacerein+Mesalazine groups compared with the DSS-induced vehicle group.

SUMMARY

In present study, the Vehicle group showed a significant increase in the DAI and colonic damage score compared with the Normal group. In addition, examination of the colon sections showed loss of crypts and epithelium and inflammatory cell infiltration of inflammatory cells in the mucosa. Thus, the DSS-induced acute colitis model in mouse was established in this study; no mortality was observed in all DSS-induced mice.

Significant body weight loss was observed with the DSS-induced vehicle group animals. Treatment with Diacerein was able to prevent the body weight loss by DSS-induction, whereas the similar effect was not observed in the Mesalazine-treated animals.

Diacerein group (30 and 60 mg/kg) and the Diaserein+Mesalazine combination groups showed significant improvement in colon length, whereas Mesalazine treatment alone groups showed only slight effect on improving colon length. The Diaserein+Mesalazine combination treatment showed significant reduction in colon-to-body weight ratio, more effective than Diacerein or Mesalazine treatment alone.

The DSS induction significantly increased the Disease activity index (DAI) than the Normal Sham group in all 5-day induction period. DAI results revealed that the treatments of Diacerein and Mesalazine on DSS-induced animals were both effective but likely exhibited different onset patterns. Mesalazine showed good effect in the first 2-3 days of treatment and gradually diminished in its activity after, while Diacerein appeared to be more effective at latter part of treatment (Day 4-5). Diacerein seemed to be more effective than Mesalazine with lower effective dose level.

Furthermore, Diacerein was shown to be superior to Mesalazine in maintaining normal body weight throughout the treatment, whereas Mesalazine had no effect in reducing body weight score. Both Diacerein and Mesalazine showed significant effects on reducing the fecal blood in these acute colitis animals. High dose of Diacerein (60 mg/kg), low dose of Mesalazine (20 mg/kg), and the Diacerein+Mesalazine combination showed significant decrease in colonic damage induced by DSS. The improvement in colonic damage score was attributable to the decrease in diarrhea score and likely thickness score, compared with the DSS-induced vehicle group.

The findings of microscopic examination of the sections of colon tissue demonstrated that the crypt and epithelium damages induced by DSS was clearly reduced with the Diacerein treatment and Diacerein+Mesalazine combination; whereas Mesalazine alone had no effect in healing the damage of intestinal membrane.

Treatment with the Mesalazine (60 mg/kg) and the Diacerein+Mesalazine combination were able to prevent the body weight loss by DSS-induction, whereas the similar effect was not observed in the Mesalazine (20 mg/kg) treated animals. The Mesalazine (20 mg/kg) and the Diacerein+Mesalazine combination groups showed significant improvement in colon weight, whereas the Mesalazine (60 mg/kg) group showed lower effect on colon weight than the DSS-induced vehicle group. The Mesalazine (20 and 60 mg/kg) treatment groups and the Diacerein+Mesalazine combination group showed significant reduction in the colon-to-body weight ratio compared with the DSS-induced vehicle group. The DSS induction significantly increased the DAI than the Normal Sham group in all 5-day induction period. DAI results revealed that the treatment of Mesalazine (60 mg/kg) and Diacerein+Mesalazine combination on DSS-induced animals was both effective.

Mesalazine showed good effect in the first 2-3 days of treatment and gradually diminished in its activity after. Especially, the diarrheal stool score and the fecal blood score were significantly decreased at Day 2 and 3. The Mesalazine (60 mg/kg) and the Diacerein+Mesalazine combination groups showed significant effects on reducing the body weight score in these acute colitis animals. The findings of microscopic examination of the sections of colon tissue demonstrated that the crypt and epithelium damages induced by DSS was clearly reduced with the Mesalazine treatments (20 and 60 mg/kg) and the Diacerein+Mesalazine combination treatment.

Treatment with the Aloe-emodin and the Aloe-emodin+Mesalazine combination were able to prevent the body weight loss by DSS-induction. The Aloe-emodin group showed significant improvement in the colon-to-body weight ratio. DAI results revealed that the treatment of the Aloe-emodin and the Aloe-emodin+Mesalazine were both effective. Both the Aloe-emodin and the Aloe-emodin+Mesalazine combination showed significant effects on reducing the body weight score in these acute colitis animals. The Aloe-emodin alone showed significant effects on reducing the fecal blood score. The Aloe-emodin+Mesalazine combination showed significant decrease in colonic damage induced by DSS. The improvement in colonic damage score was attributable to the decrease in the diarrhea score and thickness score, compared with the DSS-induced vehicle group. The findings of microscopic examination of the sections of colon tissue demonstrated that the crypt and epithelium damages induced by DSS was clearly reduced with the Aloe-emodin treatment, whereas the Aloe-emodin+Mesalazine combination had no effect in healing the damage of intestinal membrane.

Treatment with the Emodin and the Emodin+Mesalazine combination were able to prevent the body weight loss by DSS-induction. The Emodin group showed significant improvement in colon weight. The Emodin and the Emodin+Mesalazine combination groups showed significant reduction in the colon-to-body weight ratio compared with the DSS-induced vehicle group. DAI results revealed that the treatment of the Emodin and the Emodin+Mesalazine were both effective. The Emodin alone showed significant effects on reducing the body weight score, the diarrheal stool score and the fecal blood score in these acute colitis animals. The Emodin+Mesalazine combination also showed significant effects on reducing the body weight score and the fecal blood score in these acute colitis animals. The Emodin+Mesalazine combination showed significant decrease in colonic damage induced by DSS. The improvement on colonic damage score was attributable to the decrease in the thickness score and likely diarrhea score, compared with the DSS-induced vehicle group.

Treatment with the Rhein and the Rhein+Mesalazine combination were able to prevent the body weight loss by DSS-induction. The Rhein group alone showed significant improvement in colon weight. The Rhein and the Rhein+Mesalazine combination groups showed significant reduction in the colon-to-body weight ratio compared with the DSS-induced vehicle group. DAI results revealed that the treatment of the Rhein and the Rhein+Mesalazine were both effective. Both the Rhein and the Rhein+Mesalazine combination showed significant effects on reducing the body weight score in these acute colitis animals. The Rhein alone also showed significant effects on reducing the diarrheal stool score. The Rhein+Mesalazine combination group showed significant decrease in colonic damage induced by DSS. The improvement on colonic damage score was attributable to the decrease in the diarrhea score and likely thickness score, compared with the DSS-induced vehicle group. The findings of microscopic examination of the sections of colon tissue demonstrated that the crypt and epithelium damages induced by DSS was clearly reduced with the Rhein and the Rhein+Mesalazine combination treatments.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method for treating and alleviating body weight loss, colon length shortening and positive fecal occult blood symptoms associated with inflammatory bowel disease, colitis, and/or enterocolitis in a subject in need thereof, comprising the step of: administering to the subject in need thereof a composition comprising:
    (a) a therapeutically effective amount of an anthraquinone derivative selected from the group consisting of diacerein, aloe-emodin, emodin, and rhein, or a pharmaceutically acceptable salt thereof; and (b) a pharmaceutically acceptable vehicle to treat and alleviate the body weight loss, colon length shortening and positive fecal occult blood symptoms associated with the inflammatory bowel disease, colitis, and/or enterocolitis in the subject in need thereof.

2. The method of claim 1, wherein the anthraquinone derivative is diacerein.

3. The method of claim 2, further comprising the step of: administering to the subject in need thereof an additional or a second composition comprising a therapeutically effective amount of mesalazine and a pharmaceutically acceptable vehicle.

4. The method of claim 3, wherein the step of administering the composition comprising mesalazine is performed simultaneously with the step of administering the composition comprising diacerein.

5. The method of claim 3, wherein the step of administering the composition comprising mesalazine is performed in advance of the step of administering the composition comprising diacerein.

6. The method of claim 5, wherein the step of administering the composition comprising mesalazine and the step of administering the composition comprising diacerein is performed at least one day apart.

7. A method for treating and alleviating body weight loss, colon length shortening, increased colon-to-body weight ratio, diarrheal stool, positive fecal occult blood, and colonic damage symptoms associated with inflammatory bowel disease, colitis, and/or enterocolitis in a subject in need thereof, comprising: administering to the subject in need thereof a first composition comprising a therapeutically effective amount of an anthraquinone derivative selected from the group consisting of diacerein, aloe-emodin, emodin, and rhein, and a first pharmaceutically acceptable vehicle; and a second composition comprising a therapeutically effective amount of mesalazine, and a second pharmaceutically acceptable vehicle to treat and alleviate the body weight loss, colon length shortening, increased colon-to-body weight ratio, diarrheal stool, positive fecal occult blood, and colonic damage symptoms associated with the inflammatory bowel disease, colitis, and/or enterocolitis in the subject in need thereof.

8. The method of claim 7, wherein the inflammatory bowel disease, colitis, and/or enterocolitis are at least one selected from the group consisting of ulcerative colitis, Crohn's disease, acute intestinal colitis, immunotherapy-induced colitis, immunotherapy-induced enterocolitis, immune related colitis, chemotherapy-induced Colitis, taxane-induced (ischemic) colitis, chemotherapy-induced neutropenic enterocolitis, and inflamed anus or rectum.

9. The method of claim 7, wherein the colitis is at least one selected from the group consisting of microscopic colitis, diverticulosis-associated colitis, collagenous colitis, lymphocytic colitis, or Behçet's disease.

10. The method of claim 7, wherein the anthraquinone derivative is diacerein.

11. The method of claim 10, wherein the composition comprising mesalazine is administered to the subject in need thereof in advance of the composition comprising diacerein.

12. The method of claim 10, wherein the composition comprising mesalazine is administered to the subject in need thereof simultaneously with the composition comprising diacerein.

13. The method of claim 7, wherein a human daily dose of diacerein, aloe-emodin, emodin, or rhein ranges from 30 mg/kg to 60 mg/kg×$(0.020$ in kg/human weight in kg$)^{0.33}$.

14. The method of claim 1, wherein the inflammatory bowel disease, colitis, and/or enterocolitis are at least one selected from the group consisting of ulcerative colitis, Crohn's disease, acute intestinal colitis, immunotherapy-induced colitis, immunotherapy-induced enterocolitis, immune related colitis, chemotherapy-induced Colitis, taxane-induced (ischemic) colitis, chemotherapy-induced neutropenic enterocolitis, and inflamed anus or rectum.

15. The method of claim 1, wherein the colitis is at least one selected from the group consisting of microscopic colitis, diverticulosis-associated colitis, collagenous colitis, lymphocytic colitis, or Behçet's disease.

16. The method of claim 3, wherein a human daily dose of mesalazine ranges from 20 mg/kg to 100 mg/kg×$(0.020$ in kg/human weight in kg$)^{0.33}$.

17. The method of claim 1, wherein a human daily dose of diacerein, aloe-emodin, emodin, or rhein ranges from 30 mg/kg to 60 mg/kg×$(0.020$ in kg/human weight in kg$)^{0.33}$.

18. A method for treating and alleviating body weight loss, colon length shortening, increased colon-to-body weight ratio, diarrheal stool, positive fecal occult blood, and colonic damage symptoms associated with inflammatory bowel disease, colitis, and/or enterocolitis in a subject in need thereof, comprising: administering to the subject in need thereof a combination of a therapeutically effective amount of an anthraquinone derivative and a therapeutically effective amount of mesalazine, wherein the anthraquinone derivative is selected from the group consisting of diacerein, aloe-emodin, emodin, and rhein.

* * * * *